United States Patent
Lamming

(12) 
(10) Patent No.: US 6,683,071 B1
(45) Date of Patent: Jan. 27, 2004

(54) INITIATION OF OESTRUS

(75) Inventor: George Eric Lamming, Melton Mowbray (GB)

(73) Assignees: The University of Nottingham, University Park (GB); Milk Development Council, Gloucestershire (GB)

( * ) Notice: Subject to any disclaimer, the term of this patent is extended or adjusted under 35 U.S.C. 154(b) by 0 days.

(21) Appl. No.: 10/070,783

(22) PCT Filed: Sep. 6, 2000

(86) PCT No.: PCT/GB00/03423

§ 371 (c)(1), (2), (4) Date: Jul. 17, 2002

(87) PCT Pub. No.: WO01/17512

PCT Pub. Date: Mar. 15, 2001

(30) Foreign Application Priority Data

Sep. 9, 1999 (GB) .............................................. 9921341

(51) Int. Cl.$^7$ ........................ A61K 31/56; A61K 31/215
(52) U.S. Cl. ........................................ 514/177; 514/530
(58) Field of Search ................................. 514/177, 530

(56) References Cited

FOREIGN PATENT DOCUMENTS

WO        01/17512 A2  *  3/2001

OTHER PUBLICATIONS

Godke et al., "Estrus Synchronization In Cattle Using Prostaglandins", La. Agric. (1978), vol. 21 (4), pp. 12–14.*

Folman et al., "The effects of "estrumate" followed by progesterone coils on estrus synchronization and conception of post–partnum beef and diary cows," *Anim. Reprod. Sci.*, 4(2):117–126, 1981.

Johari et al., "Estrus response and fertility of suckled Kedah-Kelantan KK cows following Estrus synchronization using Cloprostenol and a progesterone–releasing intravaginal device," *Malaysian Agricultural Research and Development Institute*, 18:117–122, 1990, Abstract.

Logue et al., "A comparison of two techniques for the synchronisation of oestrus in dairy heifers," *The Veterinary Record*, 129:171–173, 1991.

Lucy et al., "Ultrasonic identification of follicular populations and return to estrus in early postpartum dairy cows given intravaginal progesterone for 15 days," *Therigenology*, 34:325–340, 1990.

Rao et al., "Estrous response and fertility in postpartum anestrous buffalos treated with a progestagen, pregnant mare serum gonadotropin and prostaglandin during the low breeding season," *Anim. Reprod. Sci.*, 8(1–2):129–135, 1985 Abstract.

Zu et al., "Reproductive performance of lactacting dairy cows following estrus synchronization regimens with pgf2a and progesterone," *Theriogenology*, 47:687–701, 1997.

* cited by examiner

*Primary Examiner*—Kevin E. Weddington
(74) *Attorney, Agent, or Firm*—Fulbright & Jaworski, LLP

(57) ABSTRACT

This invention relates to a method for the initiation of oestrus and ovulation early postpartum, especially but not exclusively, in dairy cows which comprises supplying a prostaglandin post partum and subsequently treating with a progesterone.

32 Claims, 1 Drawing Sheet

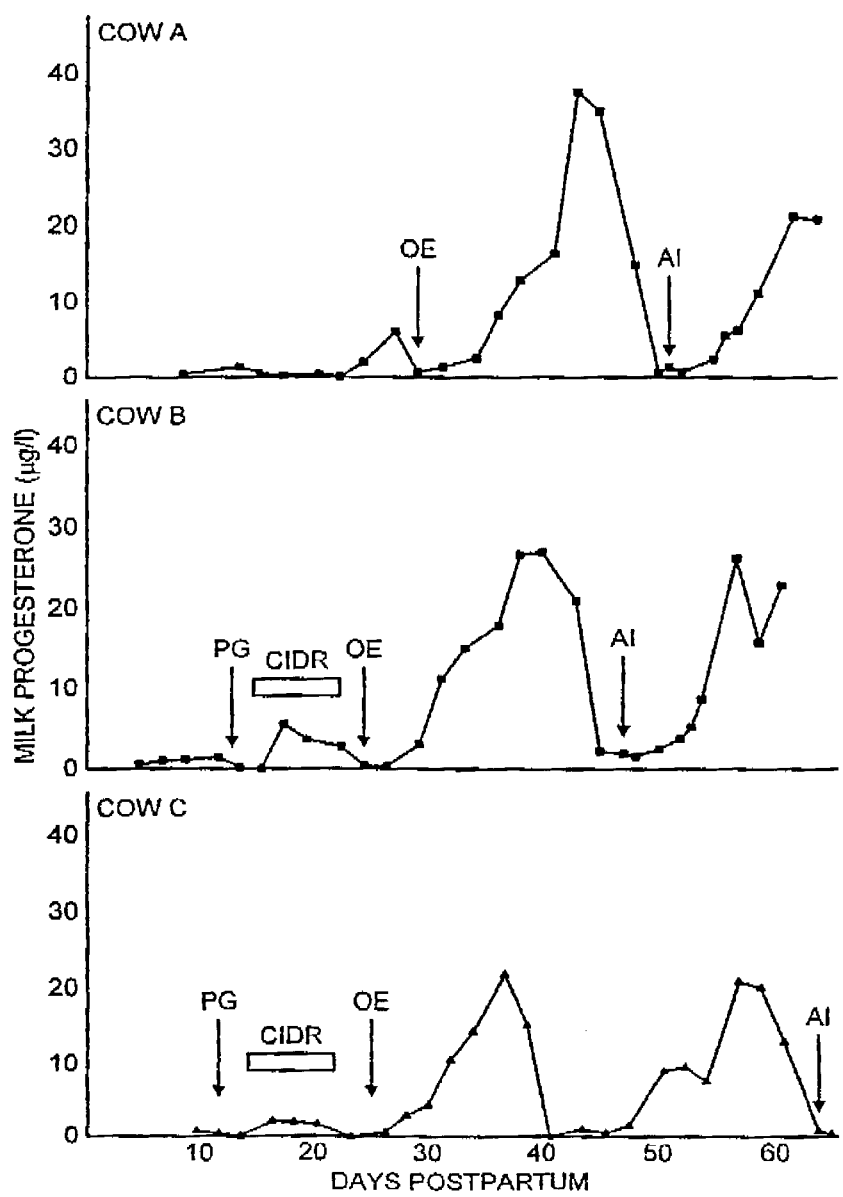

ature performance (Stevenson, J. S. and Call, E. P. (1983)

INITIATION OF OESTRUS

This application is a national stage filing under 35 U.S.C. §371 of PCT/GB00/03423, filed on Sep. 6, 2000, which claims priority to Great Britain application no. 9921341.5, filed on Sep. 9, 1999. The entire contents of both of these applications are incorporated by reference.

This invention relates to a process for the inititation of oestrus and ovulation early postpartum, especially but not exclusively, in dairy cows. The invention also relates to methods of increasing milk production.

Reproductive performance is one of the important factors determining the profitability of dairy herds. Ideally, the calving interval should average one year, but this can only be achieved if the pregnancy success and detection rate of oestus are high and the interval between parturition and first service is less than 90 days (Bulman, D. C. and Lamming G. E. J Reprod. Fert (1978) 54: 447–58).

In milked cows, there is a suppression of ovarian follicular development for a variable period after parturition and there is current evidence that a significant number of animals (about 12%) exhibit prolonged anovulatory periods postpartum (PP) (Royal, M. D., et al., (1999) Animal Science). In dairy cows there are significant changes in plasma (lutenizing hormone) LH levels after parturition, directly related to the initiation of ovarian cycles, with low basal LH levels immediately postpartum followed by increases in mean levels and the development of clear LH episodes with increasing episode frequency (Peters A. R. et al., (1981) Journal of Reproduction & Fertility 62: 567–573). There is clear evidence that the low levels of progesterone, secreted as a result of the initiation of postpartum ovarian follicular development, contribute to establishing a normal oestrous cycle pattern (Lamming, G. E., et al., (1981) Journal of Reproduction and Fertility Supplement 30: 155–170). Furthermore, the incidence of the silent ovulation in cycles prior to insemination delays the intervals to first PP insemination and conception (Senger, P. L. (1994) Journal of Dairy Science 77: 2745–2753).

There is a marked interdependence of activity between the ovaries and the uterus shortly after parturition in mammals such as cows. The early resumption of ovarian activity leading to the availability of circulating oestradiol—17β, may help to hasten uterine involution through a reduction in size, a marked increase in uterine tone (for a review see Hussein, A. M. (1989) J. Vet Med 36: 641–451) and benefits to the uterine defence mechanisms (Rowson, L. E. A. et al., (1953) Veterinary Record 65: 335–341). Similarly, the interval to post partum (PP) uterine involution is significantly correlated with the occurrence of the first PP ovulation (Madej, A. et al., (1984) Theriogenology 21: 279–287; Buch, N. C. et al., (1955) Journal of Dairy Science 38: 73–79). An early return to ovarian cyclicity PP was found by most workers to be associated with high fertility (Thatcher, W. W. and Wilcox, C. J., (1973) Journal of Dairy Science 56: 608–610; Stevenson, J. S. and Call, E. P. (1983) Theriogenology 19: 367–375; Staples, C. R et al., (990) Journal of Dairy Science 73: 938–947; Senatore, E. M. et al., (1996) Animal Science 62: 17–23; Darwash, A. O. et al., (1997) Animal Science 65: 9–16; Kinsel, M. L. and Etherington, W. G. (1998) Theriogenology 50: 1221–1238; Mann, G. E. et al., (1998) Nottingham Cattle Fertility Conference 11–12. Based on this premise, a number of workers have used prostaglandin $F_{2\alpha}$ ($PGF_{2\alpha}$) administration in an attempt to induce early postpartum uterine recovery or alternatively progesterone ($P_4$) to initiate early return to a pattern of normal oestrous cycles, but with inconsistent results. Where a prostaglandin alone has been supplied, it has been reported that a single dose of $PGF_{2\alpha}$ administered prior to day 40 postpartum is beneficial to herd fertility Young, I. M. et al., (1984) Veterinary Record 115: 429–431; Bernard, M. and Stevenson, J. S. (1986) Journal of Dairy Science 69: 800–811; Young, I. M. and Anderson, D. B. (1986) Veterinary Record 115: 429–431; Etherington, W. G. et al., (1988) Theriogenology 29: 565–575; McClary, D. G. et al., (1989) Theriogenology 31: 565–570; White, A. J. and Dobson, H. (1990) Veterinary Record 24: 588–592; Etherington, W. G. et al., (1994) Theriogenology 42: 739–752; Pankowski et al., (1995) Journal of Dairy Science 78: 1477–1488, but others have concluded that Here was no significant improvement (Mortimer et al., (1984) Theriogenology 21: 869–874; Macmillan et al., (1987) Proceeding of the New Zealand Society of Animal Production 47: 65–68; Stevenson, J. S. and Call, E. P. (1988) Journal of Dairy Science 71; 1926–1933; Armstrong et al., (1989) Veterinary Record 125: 597–600; Morton et al., (1992) Australian Veterinary Journal 69: 158–160).

Similarly, the administration of $P_4$ during the PP period is designed to initiate an early return to normal function of the hypothalamic-pituitary-ovarian axis considered necessary for the early initiation of oestrus, ovulation and luteal activity. However, the use of a progeterone-releasing intravaginal device (PRID) on Days 10 to 15 PP (Kyle, S. D. (1992) Journal of Dairy Science 75: 1456–1460 or on Days 5 to 15 PP (Stevenson, J. S. and Purseley, R. (1994) Journal of Dairy Science 77: 726–734) did not include the expected early ovulation compared with untreated animals. The latter workers reported a significant increase in the number of treated animals showing overt oestrus at the first PP ovulation compared with untreated controls (64 vs 20%).

In an attempt to improve fertility through the induction of a cyclic ovarian pattern early PP, a protocol was developed by the inventors utilising a sequence of $PGF_2$. and controlled internal drug (progesterone) release (CIDR). Prostaglandin was chosen because of its cleansing effect on the uterine environment (Gustaffson, B. et al., (1976) Theriogenology 6: 45–50; Etherington, W. G., et al., (1985) Canadian Journal of Comparative Medicine 49: 261–267) and in the promotion of uterine involution (Lindell, J. O. and Kindhal, H. (1983) Theriogenology 24: 269–274; Bonnet, B. N., et al., (1990) Theriogenology 33: 877–890) while a short period (7 days) of progesterone treatment using CIDR was designed to stimulate the short luteal phases frequently observed in PP cows (Lamming, G. E., et al., (1981) Journal of Reproduction & Fertility (Supplement) 30: 155–170; Eger, M., et al., (1988) Animal Reproductive Science 16: 215–224). Furthermore, CIDR insertion for five days was found to increase the oestrous response to subsequent $PGF_{2\alpha}$ treatment (Zu, Z. Z., et al., (1997) Theriogenology 47: 687–701).

Folman et al., (Anim. Reprod. Sci., 4, 117–26, 1981), discloses a method of synchronising oestrus in cows, wherein prostaglandin is given late post partum (after 60 days) followed by progesterone. No indication is given suggesting that by giving prostaglandin early post partum followed by progesterone that ovulation and oestrus can be initiated.

Johari et al., (Malay. Agric. Res. Dev. Inst., Res. J., 18, 117–122, 1990) discloses a method of synchronising oestrus late post partum (60–90 days) comprising giving progesterone followed by prostaglandin.

The object of the present invention is to initiate ovarian hormone cycles in cows during the early post partum period; previously claimed to be conducive to improved reproductive performance (Stevenson, J. S. and Call, E. P. (1983)

Theriogenology 19: 367–375, Darwash, A. O. et al., (1997) Animal Science 65: 9–16).

However, the concept that an early return to PP ovarian cyclicity is conducive to higher fertility has recently been challenged by Smith, M. C. A. and Wallace, J. M. (1998) Reproductive Fertility Development 10: 207–216 and their findings, albeit on a limited number of animals, merit scrutiny. These authors showed from milk $P_4$ analysis of a single herd that multiparous cows ovulating before 21 days PP exhibited poorer reproductive performance than similar animals ovulating later, an effect not observed in their primiparous cows. In the multiparous PP cows, there was a high incidence of persistent corpora lutea (PCL), a finding we have confirmed by study of a wider progesterone database involving several herds, which showed a significant increased incidence of PCL in PP cows between 1975 to 1982 and 1996 to 1998 (Royal, M. D. et al., (1999) Animal Science (in press). The incidence of PCL during the PP period has been associated with a lower submission rate for insemination, longer intervals to conception, lower pregnancy rates and a higher incidence of embryo loss and therefore, a higher culling rate (Lamming, G. E. and Darwash, A. O. (1998) Animal Reproduction Science 52: 175–190). These trends may be influenced by recent changes in the genetic structure and milk production merit of all UK dairy herds, or associated with an increased incidence of PP uterine dysfunction. The ideal scenario for maximum fertility is an early return to ovarian cyclicity in the PP cow in which the uterus has fully involuted and in the absence of uterine infection. From knowledge of the influence of a persistent uterine infection on the rate of uterine involution, a cow with a persistent uterine infection which ovulates by Day 21 postpartum may be expected to experience a delayed luteolysis, therefore a delay in the return to a normal ovarian cyclic pattern. Thus in herds where there is an increased incidence of PCL it can be expected that fertility parameters and pregnancy rates will be adversely affected. The use of intramuscular (i.m.) injection of $PGF_{2\alpha}$ in methods of the present invention is designed to decrease the chances of delayed uterine involution and persistent uterine infection.

The inventors have found that a treatment protocol typically using a single intramuscular injection of $PGF_{2\alpha}$ (Estrumate) on Days 12–14 PP followed two days later by progesterone (CIDR) for 7 days was effective in initiating ovarian cyclicity, reducing the interval to postpartum oestrus and intervals to first insemination and conception ($P<0.05$). The treatment protocol will initiate early ovarian cyclicity, improve heat detection efficiency, and therefore enhance reproductive performance, particularly in large herds using a block caving management regime.

According to one aspect of the present invention there is provided a method of initiating oestrus in a female mammal, the method comprising supplying a prostaglandin post partum and subsequently treating with progesterone or a equivalent thereof.

According to another aspect of the invention there is provided a method of increasing milk production in a female mammal, the method comprising supplying a prostaglandin or prostaglandin analogue post partum and subsequently treating with progesterone or a functional equivalent thereof There are two distinct aspects of the treatment protocol in methods according to the invention; $PGF_{2\alpha}$ injections to ensure an adequate uterine environment prior to $P_4$ administration, and $P_4$ to ensure sensitisation of the hypothalamic-pituitary-ovarian axis, to facilitate follicle development, ovulation and the manifestation of oestrus. The protocol may be applied so that animals would ovulate by Day 25 postpartum.

The mammal may be from a domesticated species, particularly a cattle species, most preferably a dairy cow.

The prostaglandin may be for example prostaglandin $PGF_{2\alpha}$ or may be a synthetic analogue thereof e.g. dinoprost, cloprostenol, luprostiol, tiaprost, etiproston tromethaline.

The prostaglandin may be supplied on any one of days 12, 13, 14 or 15 post partum. The prostaglandin may be supplied by any suitable delivery route but is preferably supplied parenterally. The term parenteral, and cognate terms, as used herein includes subcutaneous, intracutaneous, intravenous, intramuscular, intraarticular, intrasynovial, intrasternal, intrathecal, intralesional and intracranial injection or infusion techniques. Most preferably the prostaglandin is supplied by intra-muscular injection. The prostaglandin is preferably supplied at a dose of about 500 µg (or a suitable dose of analogue is supplied to give an equivalent effect).

The term "progesterone" used herein includes natural and synthetic compounds having relevant biological activity of a naturally occurring progesterone and includes progesterones isolated or derived from other species. The progesterone or progesterone equivalent may be supplied 36–60 hrs, preferably 42–54 hrs most preferably about 48 hrs after the supply of the prostaglandin.

Preferably, the progesterone is supplied by a controlled internal drug release device. The device may be in the form of a plastic intravaginal device or may be in the form of or include another controlled/sustained release system such as microcapsules, liposomes, implants, microspheres or the like.

The progesterone or progesterone equivalent may be supplied for 6 to 9 days, preferably 7 days. Where the progesterone is supplied by a controlled internal drug release device, that device may be removed after 6 to 9 days preferably after 7 days. Where the progesterone is supplied by another controlled/sustained release system that system may be arranged to stop or reduce the release of progesterone.

The progesterone may be supplied to give a milk progesterone level of 5 µg/l.

Preferred progesterone equivalents include:
flugestone acetate
medroxyprogesterone acetate
altrenogest
norgestamet According to another aspect of the invention there is supplied a kit for use in initiating oestrus in post partum mammals, or for improving milk production in mammals, the kit comprising a prostaglandin or analogue and a progesterone or an equivalent thereof. The prostaglandin may be supplied in a form for parenteral administration—preferably intramuscular injection. The progesterone or equivalent may be in a form for controlled internal release. Preferably, the progesterone or equivalent is in a form by which it can be delivered for seven days.

Preferably the kit is arranged to supply a single dose of about 500 µg of the prostaglandin $PGF_2$ or its equivalent.

The kit is preferably arranged to supply about 1.9 g of a progesterone or progesterone equivalent over the treatment period.

Methods and kits in accordance with the invention will now be described, by way of example only, with reference to the accompanying drawing, FIG. 1, which shows the effect of different treatments on levels of milk progesterone in dairy cows.

1)

a Experimental Animals and Milk Sampling

A total of 470 Holstein-Friesian cows with an average parity (number of pregnancies) of 2.4±0.08, from four farms in the East Midlands were randomly chosen either to receive hormonal treatment (T, n=155) or to serve as untreated control (C, n=315).

TABLE 1

An audit of experimental animals (n = 470)

| Farm | Control (No.) | Treated (No.) | Parity (Mean) | Calving Pattern |
|---|---|---|---|---|
| A* | 92 | 49 | 2.38 | Spring–Autumn |
| B* | 98 | 43 | 2.27 | Spring–Autumn |
| C | 60 | 45 | 2.78 | All Year |
| D | 65 | 18 | 1.88 | Extended Lactations |

*Similar breeding and feeding practices.

The cows were housed in a free-stall system and fed rations to meet their maintenance and production requirements. Data on calving date, parity, insemination date and pregnancy diagnosis were recorded. Milk samples for P4 determinations were taken three times weekly between Day 7 to Day 65 postpartum (PP) and on Days 0, 5, and 24 post insemination. All samples were placed in 30 ml plastic bottles, preserved using Lactab III tablets (Thompson and Capper Ltd., Cheshire, England) and stored at 4° C. until assayed.

a Hormonal Protocol for the Initiation of Early Cyclicity

The protocol involved a combination of two licensed drugs: a single injection i.m. of a luteolytic agent prostaglandin $F_{2\alpha}$ ($PGF_{2\alpha}$) on Days 12 to 14 PP, followed 48 hours later by an intra vaginal insertion of a progesterone releasing device remaining in situ for seven days. A synthetic $PGF_{2\alpha}$ was used (2 ml of Estrumate™ containing 500 μg of Cloprostenol, Malinkrodt Veterinary Ltd., Breakspear Road South, Harefield, Uxbridge, Middlesex UB9 6LS) and the source of progesterone was CIDR (1.9 g progesterone, InterAg, Hamilton, New Zealand).

b Oestrus Detection

In addition to the routine visual checks for oestrous behaviour, all cows were fitted with KAMAR® HEAT-MOUNT™ detectors (KAMAR, inc., Box 773838, Steamboat Springs, Colo. 80477, USA) which were replaced when the colour changed to red, usually as a result of the cow having been mounted indicating standing heat had occurred.

c Milk Progesterone Assay

Milk $P_4$ concentrations were measured in an un-extacted aliquot of whole milk by research staff using an enzyme linked immunosorbent assay (ELISA) kit (Ridgeway Science Ltd., Gloucestershire, UK) as reported by Darwash, A. O. et al., (1999) Animal Science. All samples and quality controls (QC) were assayed in duplicate and the mean value of both readings was used to indicate milk $P_4$ concentrations. Eased on QC values of 2 and 8 μg/l, the intra-and inter-assay coefficients of variation (CV) were respectively, 9.4 and 10.4% with lower and upper assay sensitivity of <1 to 23.5 μg/l. Furthermore, a routine laboratory procedure was adopted whereby all duplicate samples with milk $P_4$ values from 1.5 to 10.5 μg/l were re-assayed until the CV of the duplicate was <15%.

Statistical analysis was carried out using GLM procedure of Genstat 5.0 for Windows (Rothmstead, Berkshire, UK). Independent effects included herd, season and parity. Dependent measurements included intervals to PP commencement of oestrus, luteal activity, the incidence of silent ovulation (Days 21–65 PP), days to first PP service and days to conception. Threshold traits were analysed assuming binomial errors.

1.

a The Response to Treatment

The responses to treatment were distinguished into categories using criteria defined in Table 2 and as demonstrated in FIG. 1.

TABLE 2

Frequency and type of response to hormonal treatment in postpartum Holstein-Friesian cows (n = 153)

| Type of response | Frequency | Number (%) ovulating |
|---|---|---|
| No measurable response[1] | 12 | 5 (41.67) |
| Weak response[2] | 12 | 6 (50.00) |
| Hormonal response[3] | 70 | 58 (82.86) |
| Physiological response[4] | 18 | 17 (94.44) |
| Hormonal and Physiological | 41 | 41 (100.0) |

[1]Milk $P_4$ < 2 μg/l during CIDR treatment, not followed by oestrus.
[2]Milk $P_2$ = 2 to <3 μg/l during treatment not followed by oestrus.
[3]Milk $P_4$ > 3 μg/l during CIDR treatment not followed by oestrus.
[4]Milk $P_4$ < 3 μg/l during CIDR treatment followed by oestrus.

There were 24 (15.69%) animals which showed a weak or no-response to the insertion of CIDR while the remaining 129 (84.31%) showed either a hormonal change (increase in milk $P_4$ concentration), or a physiological response (oestus) or both responses following CIDR removal. The ovulation rate immediately following CIDR removal was significantly correlated (P<0.01) with the type of response to treatment. The ovulation rate following CIDR removal was 89.22% in 129 animals classified as having an adequate response to treatment with the highest ovulation rate (100%) occurring in animals showing measurable increases in milk $P_4$ levels, followed by behavioural oestrus.

TABLE 3

Effects of treatment on reproductive parameters in postpartum cows (n = 470)

| Group | Days to CLA[1] | Days to PP Oestrus | % in oestrus by Day 30 | % silent ovulation day 21–65 |
|---|---|---|---|---|
| Treated | 22.09 ± 0.70[a] (n = 153) | 44.91 ± 1.44[a] (n = 150) | 36.77[a] (n = 155) | 42.27[a] (N = 115) |
| Control | 29.62 ± 0.82[c] (N = 315) | 55.62 ± 1.58[c] (n = 313) | 17.72[c] (n = 315) | 56.28[c] (n = 309) |

[a,c]differ (P < 0.001)
[1]CLA = commencement of luteal activity.

As tabulated in Table 3, in addition to shortening the interval to PP commencement of luteal activity, the treatment significantly shortened the interval to PP oestrus, increased the number of animals in oestrus and ovulating by Days 30 and decreased the number of silent ovulations between days 21 to 65 PP, all at P<0.001. The precision of oestrus detection was enhanced by using KAMAR® heat mount detectors in addition to progesterone monitoring and the herdsman's routine observations.

The effects of herd, seasons and parity on the response to treatment is shown in Table 4.

TABLE 4

Significance levels of the effects on reproductive parameters included in the statistical analysis model

| Effects | Reproductive Parameters | | | | | |
|---|---|---|---|---|---|---|
| | A | B | C | D | E | F |
| Herd (H) | | *** | *** | * | *** | |
| Season (S) | | | | * | | |
| Parity (P) | | *** | *** | *** | * | |
| Treatment (T) | *** | ** | ** | | * | |
| HXS | * | | | | | |
| HXP | * | | | | *** | |
| SXP | | | * | | ** | |
| HXT | | | | | | |
| SXT | | * | | | | |
| PXT | | | ** | * | * | |
| HXSXP | | | | | | |
| HXSXT | | | | | | |
| HXPXT | | | | | | |
| SXPXT | | | | | | |
| HXSXPXT | | | | | | |

A = Days to PP commencement of luteal activity (as defined by a level of milk progestrone > 3 μg/ml)
B = Days to PP oestrus
C = Incidence (%) of silent ovulation on Days 21–65 PP
D = Days PP to 1st PP service
E = Days to PP conception
F = Number of services per conception
*P < 0.05.
**P < 0.001
***P < 0.001

Although there was no significant effects of herd or parity on the interval to CLA (Parameter A), there were significant herd and parity effects on the interval to PP oestrus (Parameter B), interval to PP service (Parameter D) and days to conception (Parameter E).

Treatment was effective (P<0.001) in reducing the mean interval to postpartum commencement of luteal activity from 29.62±0.82 d to 22.09±0.70 d. The mean interval to first PP oestrus in the (Treated) T animals was significantly reduced (p<0.001) from 55.62±1.58 d to 44.91±1.44 d and the incidence of silent ovulation in cycles between Days 21 to 65 PP was reduced (P<0.001) from 56.28% to 42.27%. In two herds under one management and with a similar block-calving pattern (n=282 animals), the treatment protocol was beneficial to the overall reproductive performance as there was a significant shortening in the mean interval to first PP service (75.82±1.93 vs 80.86a±1.32d) and in the interval to PP conception (83.07±2.49d vs 88.90±1.95), both P<0.05.

The fertility parameters for herds C and D (Table 1) were prejudiced by the management approach to breeding policy which made it impossible to assess the effects of treatment on the reproductive performance of cows in these herds. Consequently, analysis of the effects of treatment on fertility was limited to cows in herds A and B; as they were on the same estate, with comparable parities and managed by a single management system. As shown in Table 5, the treatment protocol has significantly (P<0.05) shortened the interval to PP service and conception without affecting the number of services per conception

TABLE 5

The efficacy of hormonal treatment in the initiation of cyclidty and subsequent fertility in postpartum (PP) cows in Herds A and B.

| Group | Days to PP CLA | Days to PP oestrus | Days to PP service | Days to conception | Services per conception |
|---|---|---|---|---|---|
| Treated (n = 90) | 20.87 ± 0.86$^a$ | 35.90 ± 1.70$^a$ | 75.82 ± 1.93$^a$ | 83.07 ± 2.49$^a$ | 1.32 ± 0.07$^{NS}$ |
| Control (190) | 30.08 ± 1.09$^b$ | 51.67 ± 1.81$^c$ | 80.86 ± 1.32$^b$ | 88.90 ± 1.95$^b$ | 1.29 ± 0.05$^{NS}$ |

$^{a,b}$P < 0.05
$^{a,c}$P < 0.001,
CLA = Commencement of Luteal activity.

In summary, Eight percent of animals (Table 2) showed no increase in milk $P_4$ concentrations during treatment. The remaining animals (92%) showed an increased milk $P_4$ concentration during CIDR treatment and also a clear response within one week of CIDR removal; either a physiological response by manifestation of oestrus or a hormonal response as shown by the increased concentrations of milk progesterone ($P_4$ 3 μg/l) indicating that ovulation had occurred (see FIG. 1). There was a considerable variation among the cows in milk $P_4$ concentrations during CIDR treatment as previously demonstrated in ovariectomised cows by Van Cleeff, J. et al., (1992) *Animal Reproduction Science* 27: 91–106 and considered the result of variation in metabolism of progesterone absorbed from the CIDR.

The method of the invention successfully decreased the interval to postpartum commencement of luteal activity and as a result it decreased the number of days to PP oestrus. It increased the incidence of overt oestrus at both the subsequent and later ovulations up to Day 65 PP also observed by Stevenson, J. S. and Pursely, R. (1994) *Journal of Dairy Science* 77: 725–734. The work of the inventors confirms that progesterone is important in regulating hypothalamic-pituitary-ovarian activity, thus predisposing the treated postpartum animals more likely to exhibit behavioral oestrus prior to ovulation. There is a general consensus that oestradiol arising from follicular maturation is more effective in inducing oestrus when progesterone has pre-sensitised the brain to its action. It also acts on the hypothalamic pituitary axis to increase the synchrony between pulses of LH an FSH to induce full ovarian cyclicity (Williams, G. L. et al., (1983) *Biology of Reproduction* 29: 362–373; Stevenson, J. S. and Pursely, R. (1994) *Journal of Dairy Science* 77: 725–734). Table 4 shows the significance of the effects of herd and parity On the various parameters studied In studying the direct effects of treatment of fertility parameters, the analysis was confined to pooled data from two herds (A and B); both on one estate, under the same management and feeding regimes and using a block calving pattern. The management objective was to concentrate the calving pattern during the spring and autumn. The treatment in these herds improved overall reproductive performance compared to controls, significantly decreasing the days to PP service and days to conception without influencing the number of services per conception (see Table 5). The early cyclic ovarian pattern and higher incidence of overt oestrus induced by the treatment protocol helped to increase the percentage of animals inseminated during the first three weeks of the breeding period and reduced the need of veterinary intervention (Dally, A. E. H. (1997) *Cattle Practice* 5: 371. Thus the initiation of early ovarian cyclicity in these two herds resulted in an improved reproductive performance which is in agreement with that reported by Stevenson, J. S. and Call, E. P. (1983) *Theriogenology*, 19: 367–375; Darwash, A. O. et al., (1997) *Animal Science* 65: 9–16 in dairy cows and the findings of Mann, G. E. et al., (1998) *Nottingham Cattle Fertility Conference* 11–12 in beef cows.

What is claimed is:

1. A method of initiating oestrus in a female mammal, the method comprising supplying a prostaglandin or prostaglandin analogue early post partum and subsequently treating with a progesterone or progesterone equivalent.

2. A method of increasing milk production in a female mammal, the method comprising supplying a prostaglandin or prostaglandin analogue post partum and subsequently treating with a progesterone or progesterone equivalent.

3. A method according to claim 1 in which the mammal is from a domesticated species.

4. A method according to claim 3 in which the mammal is from a cattle species.

5. A method according to claim 4 in which the mammal is a dairy cow.

6. A method according to claim 1 in which the prostaglandin is prostaglandin $PGF_{2\alpha}$.

7. A method according to claim 1 in which the prostaglandin or prostaglandin analogue is supplied on one or more of days 12, 13, 14 or 15 postpartum.

8. A method according to claim 1 in which the prostaglandin or prostaglandin analogue is supplied by parenteral administration.

9. A method according to claim 8 in which the prostaglandin or prostaglandin analogue is supplied by intramuscular injection.

10. A method according to claim 1 in which the prostaglandin or prostaglandin analogue is supplied at a dose of about 500 µg.

11. A method according to claim 1 in which the progesterone or progesterone equivalent is supplied from about 36 to 60 hours after the supply of the prostaglandin or prostaglandin analogue.

12. A method according to claim 11 in which the progesterone or progesterone equivalent is supplied from about 42 to 54 hours after the supply of the prostaglandin or prostaglandin analogue.

13. A method according to claim 12 in which the progesterone or progesterone equivalent is supplied from about 48 hours after the supply of the prostaglandin or prostaglandin analogue.

14. A method according to claim 1 in which the progesterone or progesterone equivalent is supplied by a controlled internal drug release device.

15. A method according to claim 1 in which the progesterone or progesterone equivalent is supplied for about 6 to 9 days.

16. A method according to claim 15 in which the progesterone or progesterone equivalent is supplied for 7 days.

17. A method according to claim 14 in which the controlled internal drug release device is removed after 6 to 9 days.

18. A method according to claim 17 in which the controlled internal drug release device is removed after about 7 days.

19. A method according to claim 1 in which the progesterone or progesterone equivalent is supplied to give a milk progesterone level in the mammal of about 5 µg/l.

20. A method according to claim 1 in which the mammal ovulates by about day 25 postpartum.

21. A kit for use in initiating oestrus in a post partum mammal or for increasing milk products in a mammal comprising a prostaglandin or prostaglandin analogue for initial supply to the mammal and a progesterone or progesterone equivalent for subsequent supply to the mammal, wherein the prostaglandin or prostaglandin analogue is to be delivered early post partum.

22. A kit according to claim 21 in which the prostaglandin or prostaglandin analogue is in a form which is suitable for parenteral administration.

23. A kit according to claim 22 in which the prostaglandin or prostaglandin analogue is for intramuscular injection.

24. A kit according to claim 21 in which the progesterone or progesterone equivalent is in a form for controlled internal release.

25. A kit according to claim 24 in which the controlled internal release form causes progesterone or progesterone equivalent to be delivered for 6 to 9 days.

26. A kit according to claim 25 in which the controlled internal release form causes progesterone or progesterone equivalent to be delivered for about 7 days.

27. A kit according to claim 21 arranged to supply a single dose of about 500 µg of the prostaglandin or prostaglandin.

28. A kit according to claim 21 containing about 1.9 g of a progesterone or progesterone equivalent.

29. A method according to claim 1 in which the prostaglandin analogue is cloprostenol, dinoprost, tiaprost, luprostiol, or etiproston tromethamine.

30. A method according to claim 1 in which the progesterone equivalent is flugestone acetate, medroxyprogesterone acetate, altrenogest, or norgestamet.

31. A kit according to claim 21 in which the prostaglandin analogue is cloprostenol, dinoprost, tiaprost, luprostiol, or etiproston tromethamine.

32. A kit according to claim 21 in which the progesterone equivalent is flugestone acetate, medroxyprogesterone acetate, altrenogest, or norgestamet.

* * * * *